United States Patent
Beatch et al.

(10) Patent No.: US 6,740,673 B2
(45) Date of Patent: *May 25, 2004

(54) QUARTERNARY AMMONIUM COMPOUNDS

(75) Inventors: Gregory N. Beatch, British Columbia (CA); Lewis S. L. Choi, British Columbia (CA); Clive P. Page, London (GB); Bertrand M. C. Plouvier, British Columbia (CA); Yuzhong Liu, British Columbia (CA)

(73) Assignee: UCB Farchim SA, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 10/144,607

(22) Filed: May 13, 2002

(65) Prior Publication Data

US 2002/0165402 A1 Nov. 7, 2002

Related U.S. Application Data

(62) Division of application No. 09/328,541, filed on Jun. 9, 1999, now Pat. No. 6,388,095.
(60) Provisional application No. 60/088,587, filed on Jun. 9, 1998.

(51) Int. Cl.$^7$ ..................... A61K 31/404; C07D 209/08
(52) U.S. Cl. ........................................ 514/414; 548/455
(58) Field of Search ........................... 514/414; 548/455

(56) References Cited

U.S. PATENT DOCUMENTS

| | | | |
|---|---|---|---|
| 3,529,062 A | 9/1970 | Renner | ........................ 424/274 |
| 3,769,299 A | 10/1973 | Landgraf et al. | ....... 548/519 X |
| 6,388,095 B1 * | 5/2002 | Beatch et al. | |

FOREIGN PATENT DOCUMENTS

| | | |
|---|---|---|
| DE | 2825192 | 12/1979 |
| WO | 99-64398 | 12/1999 |

* cited by examiner

Primary Examiner—Joseph K. McKane
Assistant Examiner—Sonya Wright
(74) Attorney, Agent, or Firm—Nields & Lemack (57) ABSTRACT

Novel compounds and pharmaceutical compositions containing such compounds and possessing anti-tussive activity, and a method of administering the same to warm-blooded animals, including humans.

2 Claims, 2 Drawing Sheets

QUARTERNARY AMMONIUM COMPOUNDS

This application is a divisional of U.S. application Ser. No. 09/328,541, filed Jun. 9, 1999, now U.S. Pat. No. 6,388,095, which claims the benefit of Provisional Application No. 60/088,587, filed Jun. 9, 1998.

BACKGROUND OF THE INVENTION

Conventional cough preparations containing an effective anti-tussive agent such as codeine have long been used for the symptomatic relief of coughs. However, codeine has various side effects which are undesirable.

Accordingly, the present invention relates to compounds and pharmaceutical compositions having anti-tussive activity, and a method of treating warm-blooded animals affected by coughs by administering an effective amount of the compounds or the pharmaceutical compositions of the invention.

SUMMARY OF THE INVENTION

The problems of the prior art have been overcome by the present invention, which provides pharmaceutical compositions possessing anti-tussive activity, and a method of administering the same to warm-blooded animals, including humans. The active anti-tussive agent in accordance with the present invention is a novel quarternary ammonium compound represented by the following formula (I), or a solvate or pharmaceutically acceptable salt thereof:

(I)

wherein Y and E are independently selected from —$CH_2$—$R_{16}$ or a group represented by the following formula (II):

(II)

wherein R, $R_1$, $R_2$, $R_3$, $R_4$, $R_5$, $R_6$ and $R_{16}$ are independently selected from hydrogen, $C_1$–$C_8$ alkyl, $C_3$–$C_8$ alkoxyalkyl and $C_7$–$C_{11}$ aralkyl; m is an integer of from 1 to 8 and n is an integer of from 0 to 8; A is selected from $C_5$–$C_{12}$ alkyl, a $C_3$–$C_{13}$ carbocyclic ring, and ring systems selected from formulae (III), (IV), (V), (VI), (VII), (VIII), (IX) and (X):

(III)

(IV)

(V)

(VI)

(VII)

(VIII)

(IX)

(X)

where $R_7$, $R_8$, $R_9$, $R_{10}$, $R_{11}$ and $R_{12}$ are independently selected from bromine, chlorine, fluorine, carboxy, hydrogen, hydroxy, hydroxymethyl, methanesulfonamido, nitro, sulfamyl, trifluoromethyl, $C_2$–$C_7$ alkanoyloxy, $C_1$–$C_6$ alkyl, $C_1$–$C_6$ alkoxy, $C_2$–$C_7$ alkoxycarbonyl, $C_1$–$C_6$ thioalkyl, aryl and N($R_{13}$, $R_{14}$) where $R_{13}$ and $R_{14}$ are independently selected from hydrogen, acetyl, methanesulfonyl and $C_1$–$C_6$ alkyl, and Z is selected from CH, $CH_2$, O, N and S, where Z may be directly bonded to X when Z is CH, or X may be a direct bond to Z when Z is N, or Z may be directly bonded to $R_{15}$ when Z is N and X is not a direct bond to Z, $R_{15}$ is selected from hydrogen, $C_1$–$C_6$ alkyl, $C_5$–$C_8$ cyclocalkyl, aryl and benzyl; and X is N—Re except when Z in A is nitrogen and X is a direct bond to Z; An is the acid addition salt of a pharmaceutically acceptable acid or the anion from a pharmaceutically acceptable salt, and isolated enantiomeric, diastereomeric and geometric isomers thereof, and mixtures thereof, with the proviso that Y and E cannot both be —$CH_2$—$R_{16}$ in the same compound[, and when Y is represented by formula (II) where n is 0, m is 1, $R_2$ and $R_3$ are each hydrogen, X is N—H and A is represented by formula (III), then E is not —$CH_2$—$R_{16}$ or the same as Y].

Within the respiratory tract the epithelium of the larynx, trachea, and larger bronchi contains sensory nerves that are responsible for cough. Coughing is initiated when sensory receptors in the respiratory tract receive stimuli of sufficient intensity to evoke an increase in afferent nerve impulse activity. Cough reflexes can be provoked easily by mechanical and chemical stimuli applied to the epithelium of either the larynx or tracheobronchial tree. There are three main groups of airway sensory receptors which may be involved in the cough reflex initiated from these sites: the slowly adapting stretch receptors, the rapidly adapting (irritant) receptors (RARs), and the pulmonary and bronchial C-fibre receptors. Each is distributed throughout the tracheobronchial tree and the last group is also present in the alveolar wall. Irritant and C-fibre receptors have also been identified in the larynx. Stimulation of irritant receptors evokes the cough reflex; stimulation of the C-fibre receptors may either evoke or inhibit the cough reflex; stimulation of the slowly adapting stretch receptors may facilitate the cough reflex.

Drugs which inhibit cough may act at a variety of sites, both peripherally and centrally. For example, it is generally assumed that the anti-tussive efects of currently available opiates are mediated centrally through an action on the 'cough centre' in the medulla (D. T. Chou et al. J. Pharmacol. Exp. Ther. 1975, 194, 499). Thus the number of potential sites of action of anti-tussive drugs includes all components of the cough reflex pathway, from its initiation to its final synchronized motor response.

It has now been discovered that a class of cation channel modulator/blockers are of potential use in the treatment and/or prevention of cough in warm-blooded animals including humans. The cation channel modulator/blockers of the present invention inhibit the initiation of an action potential by a cation channel at the peripheral fine afferent nerve ending or on peripheral sensory neuron that is responsible for inducing cough or triggering cough reflex. The cation channel at peripheral fine afferent nerve ending or on peripheral sensory neuron may be coupled as the transduction mechanism to one or more sensory receptors described above (RARs, C-fibre receptors and the slowly adapting stretch receptors).

The cation channel at the peripheral fine afferent nerve ending or peripheral sensory neuron is identified to be a member of the acid-sensing ion channels (ASIC) or the dorsal root acid-sensing ion channel (DRASIC). (see e.g. R. Waldmann et al. Curr. Opin. Neurobiol. 1998, 8(3), 418).

In another embodiment, the present invention provides the cation channel modulator/blockers that are quaternary ammonium compounds.

In another embodiment, the present invention provides the cation channel modulator/blockers that are quaternary ammonium compounds of formula I.

In another embodiment, the present invention provides a method for the treatment and/or prevention of cough in warm-blooded animals including human, which comprises administering to a warm-blooded animal in need thereof a therapeutically effective amount of an antitussive comprising as the antitussive effective ingredient a modulator/blocker of a cation channel, or a pharmaceutically acceptable salt thereof.

In another embodiment, the present invention provides a method for the treatment and/or prevention of cough in warm-blooded animals including human, which comprises administering to a warm-blooded animal in need thereof a therapeutically effective amount of an antitussive comprising as the antitussive effective ingredient a modulator/blocker of a cation channel that is at the peripheral fine afferent nerve ending or on a peripheral sensory neuron of said warm-blooded animal, or a pharmaceutically acceptable salt thereof.

In yet another embodiment, the present invention provides a method for the treatment and/or prevention of cough in warm-blooded animals including human, which comprises administering to a warm-blooded animal in need thereof a therapeutically effective amount of an antitussive comprising as the antitussive effective ingredient a modulator/blocker of a cation channel that is at the peripheral fine afferent nerve ending or on a peripheral sensory neuron which may be coupled as the transduction mechanism to one or more sensory receptors of said warm-blooded animal, or a pharmaceutically acceptable salt thereof.

In still another embodiment, the present invention provides a method for the treatment and/or prevention of cough in warm-blooded animals including human, which comprises administering to a warm-blooded animal in need thereof a therapeutically effective amount of an antitussive comprising as the antitussive effective ingredient a modulator/blocker of a cation channel that inhibits initiation of an action potential at the peripheral fine afferent nerve ending or on a peripheral sensory neuron of said warm-blooded animal, or a pharmaceutically acceptable salt thereof.

In yet another embodiment, the present invention provides a method for the treatment and/or prevention of cough in warm-blooded animals including human, which comprises administering to a warm-blooded animal in need thereof a therapeutically effective amount of an antitussive comprising as the antitussive effective ingredient a modulator/blocker of a cation channel that inhibits initiation of an action potential at the peripheral fine afferent nerve ending or on a peripheral sensory neuron that is responsible for inducing cough or triggering cough reflex of said warm-blooded animal, or a pharmaceutically acceptable salt thereof.

In still another embodiment, the present invention provides a method for the treatment and/or prevention of cough in warm-blooded animals including human, which comprises administering to a warm-blooded animal in need thereof a therapeutically effective amount of an antitussive comprising as the antitussive effective ingredient a modulator/blocker of a cation channel that inhibits from extracellular loci the initiation of an action potential at the peripheral fine afferent nerve ending or on a peripheral sensory neuron that is responsible for inducing cough or triggering cough reflex of said warm-blooded animal, or a pharmaceutically acceptable salt thereof.

In still another embodiment, the present invention provides a method for the treatment and/or prevention of cough in warm-blooded animals including human, which comprises administering to a warm-blooded animal in need thereof a therapeutically effective amount of an antitussive comprising as the antitussive effective ingredient a modulator/blocker of an acid-sensing ion channel (ASIC), or a pharmaceutically acceptable salt thereof.

In yet another embodiment, the present invention provides a method for the treatment and/or prevention of cough in warm-blooded animals including human, which comprises administering to a warm-blooded animal in need thereof a therapeutically effective amount of an antitussive comprising as the antitussive effective ingredient a modulator/blocker of a dorsal root acid-sensing ion channel (DRASIC), or a pharmaceutically acceptable salt thereof.

In still another embodiment, the present invention provides a method for the treatment and/or prevention of cough in warm-blooded animals including human, which comprises administering to a warm-blooded animal in need thereof a therapeutically effective amount of an antitussive comprising as the antitussive effective ingredient a modulator/blocker of an acid-sensing ion channel (ASIC) at the peripheral fine afferent nerve ending or on a peripheral sensory neuron, or a pharmaceutically acceptable salt thereof.

In still another embodiment, the present invention provides a method for the treatment and/or prevention of cough in warm-blooded animals including human, which comprises administering to a warm-blooded animal in need thereof a therapeutically effective amount of an antitussive comprising as the antitussive effective ingredient a modulator/blocker of an acid-sensing ion channel (ASIC) at the peripheral fine afferent nerve ending or on a peripheral sensory neuron which may be coupled as the transduction mechanism to one or more sensory receptors, or a pharmaceutically acceptable salt thereof.

In yet another embodiment, the present invention provides a method for the treatment and/or prevention of cough in warm-blooded animals including human, which comprises administering to a warm-blooded animal in need thereof a therapeutically effective amount of an antitussive comprising as the antitussive effective ingredient a quaternary ammonium compound functioning as a modulator/blocker of an acid-sensing ion channel (ASIC) at the peripheral fine afferent nerve ending or on a peripheral sensory neuron, or a pharmaceutically acceptable salt thereof.

In yet another embodiment, the present invention provides a method for the treatment and/or prevention of cough in warm-blooded animals including human, which comprises administering to a warm-blooded animal in need thereof a therapeutically effective amount of an antitussive comprising as the antitussive effective ingredient a quaternary ammonium compound of Formula (I) functioning as a modulator/blocker of an acid-sensing ion channel (ASIC) at the peripheral fine afferent nerve ending or on a peripheral sensory neuron, or a pharmaceutically acceptable salt thereof.

DETAILED DESCRIPTION OF THE INVENTION

As used herein, the following terms have the following meaning:

"Alkyl" refers to a branched or unbranched hydrocarbon fragment containing the specified number of carbon atoms and having one point of attachment. Examples include n-propyl A $C_3$ alkyl), isopropyl (also a $C_3$ alkyl) and t-butyl (a $C_4$ alkyl).

"Alkoxyalkyl" refers to an alkylene group substituted with an alkoxy group. For example, methyoxyethyl ($CH_3OCH_2CH_2$—) and ethoxymethyl ($CH_3CH_2OCH_2$—) are both $C_3$ alkoxyalkyl groups.

"Alkylene" refers to a divalent radical which is a branched or unbranched hydrocarbon fragment containing the specified number of carbon atoms and having two points of attachment. An example is propylene (—$CH_2CH_2CH_2$—), a $C_3$ alkylene.

"Aralkyl" refers to an alkylene group wherein one of the points of attachment is to an aryl group. An example is the benzyl group ($C_6H_5CH_2$—), a $C_7$ aralkyl group.

"Alkanoyloxy" refers to an ester substituent wherein the ether oxygen is the point of attachment to the molecule. Examples include propanoyloxy ($CH_3CH_2C(O)$—O—), a $C_3$ alkanoyloxy and ethanoyloxy ($CH_3C(O)$—O), a $C_2$ alkanoyloxy.

"Alkoxy" refers to an O-atom substituted by an alkyl group, for example methoxy (—$OCH_3$), a $C_1$ alkoxy.

"Alkoxycarbonyl" refers to an ester substituent wherein the carbonyl carbon is the point of attachment to the molecule. Examples include ethoxycarbonyl ($CH_3CH_2(O)C=O$), a $C_3$ alkoxycarbonyl, and methoxycarbonyl ($CH_3OC(O)$—), a $C_2$ alkoxycarbonyl.

"Aryl" refers to aromatic groups which have at least one ring having a conjugated pi electron system and includes carbocyclic aryl, heterocyclic aryl (also known as heteroaryl groups) and biaryl groups, all of which may be optionally substituted. Carbocyclic aryl groups are generally preferred in the compounds of the present invention, wherein phenyl and naphthyl groups are preferred carbocyclic aryl groups.

"Cycloalkyl" refers to a ring, which may be saturated or unsaturated and monocyclic, bicyclic or tricyclic formed entirely from carbon atoms. An example is the cyclopentenyl group ($C_5H_7$—), which is a five carbon unsaturated cycloalkyl group.

"Carbocyclic" refers to a ring which may be either an aryl ring or a cycloalkyl ring, both as defined above.

"Thioalkyl" refers to a sulfur atom substituted by an alkyl group, for example thiomethyl ($CH_3S$—), a $C_1$ thioalkyl.

The origin of the cough to be treated by the present invention is not particularly limited, and can include virtually any respiratory disorder, such as chronic obstructive pulmonary disease, tuberculosis, bronchitis, respiratory malignancies, asthma, allergy, pulmonary fibrosis, respiratory tract inflammation, emphysema, pneumonia, lung cancer, presence of foreign bodies, soar throat, common cold, influenza, respiratory tract infection, bronchoconstriction, inhalation of irritants, smoker's cough, chronic non-productive cough, neoplastic cough, cough due to angiotension converting enzyme (ACE) inhibitor therapy, etc. Cough may also occur without a known cause.

The compounds of the present invention are quaternary ammonium salts represented by the following formula (I), or a solvate or pharmaceutically acceptable salt thereof:

(I)

wherein Y and E are independently selected from —$CH_2$— $R_{16}$ or a group represented by the following formula (II):

(II)

wherein R, $R_1$, $R_2$, $R_3$, $R_4$, $R_5$, $R_6$ and $R_{16}$ are independently selected from hydrogen, $C_1$–$C_8$ alkyl, $C_3$–$C_8$ alkoxyalkyl and $C_7$–$C_{12}$ aralkyl; m is an integer of from 1 to 8 and n is an integer of from 0 to 8; A is selected from $C_5$–$C_{12}$ alkyl, a $C_3$–$C_{13}$ carbocyclic ring, and ring systems selected from formulae (III), (IV), (V), (VI), (VII), (VIII), (IX) and (X):

(III)

(IV)

(V)

(VI)

(VII)

(VIII)

(IX)

(X)

where $R_7$, $R_8$, $R_9$, $R_{10}$, $R_{11}$ and $R_{12}$ are independently selected from bromine, chlorine, fluorine, carboxy, hydrogen, hydroxy, hydroxymethyl, methanesulfonamido, nitro, sulfamyl, trifluoromethyl, $C_2$–$C_7$ alkanoyloxy, $C_1$–$C_6$ alkyl, $C_1$–$C_6$ alkoxy, $C_2$–$C_7$ alkoxycarbonyl, $C_1$–$C_6$ thioalkyl, aryl and $N(R_{13}, R_{14})$ where $R_{13}$ and $R_{14}$ are independently selected from hydrogen, acetyl, methanesulfonyl and $C_1$–$C_6$ alkyl, and Z is selected from CH, $CH_2$, O, N and S, where Z may be directly bonded to X when Z is CH, or X may be a direct bond to Z when Z is N, or Z may be directly bonded to $R_{15}$ when Z is N and X is not a direct bond to Z, $R_{15}$ is selected from hydrogen, $C_1$–$C_6$ alkyl, $C_3$–$C_8$ cyclocalkyl, aryl and benzyl; and X is N—$R_6$ except when Z in A is nitrogen and X is a direct bond to Z; $An^-$ is the acid addition salt of a pharmaceutically acceptable acid or the anion from a pharmaceutically acceptable salt, and isolated enantiomeric, diastereomeric and geometric isomers thereof, and mixtures thereof, with the proviso that Y and E cannot both be —$CH_2$—$R_{16}$ in the same compound[, and when Y is represented by formula (II) where n is 0, m is 1, $R_2$ and $R_3$ are each hydrogen, X is N—H and A is represented by formula (III)

the E is not —$CH_2$—$R_{16}$ or the same as Y].

A preferred compound of the present invention is a compound of the formula (I) as represented by N,N-Bis-[(1-Indolinyl)carbonylmethyl]dimethylammonium chloride with the following structure:

Another preferred compound of the present invention is a compound of the formula (I) as represented by N-[(1-Indolinyl)carbonylmethyl]-N-(phenylcarbamoylmethyl)dimethylammonium chloride with the following structure:

Another preferred compound of the present invention is a compound of the formula (I) as represented by N-[(1-Indolinyl)carbonylmethyl]triethylammonium chloride with the following structure:

Another preferred compound of the present invention is a compound of the formula (I) as represented by N,N-Bis-[(1-Naphthyl)carbonylmethyl]dimethylammonium chloride with the following structure:

The compounds of the present invention may be prepared by analogy with known synthetic methodology (see, e.g., Belgian Patent 614,154, which follows from Swedish Patent 1779/71, the disclosures of which are herein incorporated by reference). A conventional route of synthesis involves three steps and can be described (as in the aforementioned patent, see also T. Takahashi, J. Okada, M. Hori, A. Kato, K. Kanematsu, and Y. Yamamoto, *J. Pharm. Soc. Japan* 76, 1180–6 (1956)) as follows.

In a first step an aromatic amine is reacted with chloracetyl chloride in a suitable solvent such as dichloromethane and in the presence of triethylamine. The reaction is conducted at low temperature (−15° C.) and the desired product is recovered from the reaction mixture by conventional organic chemistry techniques, and if necessary, can be purified by chromatography techniques. In a second step, the above chlorinated derivative can be reacted with a tertiary amine in a solvent such as methanol with a catalyst (e.g., potassium iodide) to form a quaternary ammonium salt. The chlorinated intermediate can react as well with a secondary amine to provide the corresponding tertiary amine, which is then further reacted with a chlorinated derivative to form a quaternary ammonium salt.

The synthetic procedures described herein, especially when taken with the general knowledge in the art, provide sufficient guidance to those of ordinary skill in the art to perform the synthesis, isolation, and purification of the compounds of the present invention.

Suitable pharmaceutically acceptable salts include acid addition salts of acids such as hydrochloric, hydrobromic, benzenesulfonic (besylate), benzoic, camphorsulfonic, ethanesulfonic, fumaric, gluconic, glutamic, isethionic, maleic, malic, mandelic, methanesulfonic, mucic, nitric, pamoic, pathothenic, succinic, p-toluenesulfonic, phosphoric, sulphuric, citric, tartaric, lactic and acetic acid, although the preferred acid addition salt is the hydrochloride salt.

The magnitude of the therapeutic or prophylactic dose of the compounds of the present invention in the treatment and/or prevention of cough will depend upon the severity and nature of the condition being treated and the route of administration. The dose and the frequency of the dosing will also vary according to age, body weight and response of the individual patient. In general, the total daily dose range for the compounds of the present invention for the treatment or prevention of cough is from about 0.1 to about 800 mg in single or repeated doses.

Any suitable route of administration may be employed to provide an effective dosage of the compounds of the present invention, although administration by inhalation is preferred, most preferably in aerosol form. Suitable forms of administration include, but are not limited to, inhalation (delivered by, e.g., metered-dose inhaler, jet nebulizer, ultrasonic nebulizer, dry powder inhaler, etc.), nasal sprays, nebulization, oral administration such as via tablets, capsules, lozenges, syrups, sprays, suspensions, elixirs, gargles, and other liquid preparations, aerosol foams, parental administration, and sublingual administration.

The compounds of the present invention can include pharmaceutically acceptable carriers and other conventional additives, including aqueous based carriers, co-solvents such as ethyl alcohol, propylene glycol and glycerin, fillers, lubricants, wetting agents, flavoring agents, coloring agents, emulsifying, suspending or dispersing agents, suspending agents, etc. For aerosol delivery of the compounds of the present invention, pharmaceutically acceptable diluents, carriers, and/or propellants may be included in the formulations for use in appropriate devices. These are prepared by procedures well known to those skilled in the art (see e.g., Medication Teaching Manual, 5th Ed., Bethesda, Md., American Society of Hospital Pharmacists, 1991).

The compositions of the present invention may optionally include other known therapeutic agents, including decongestants such as pseudoephedrine HCl, phenylephrine HCl and ephedrine HCl, non-steroidal anti-inflammatory drugs such as acetaminophen, aspirin, phenacetin, ibuprofen and ketoprofen, expectorants such as glyceryl guaiacolate, terpin hydrate and ammonium chloride, antihistamines such as chlorpheniramine maleate, doxylamine succinate, brompheniramine maleate and diphenhydramine hydrochloride, and anesthetic compounds such as phenol.

The following examples are offered by way of illustration and not by way of limitation.

EXAMPLE 1

N,N-Bis-[(1-Indolinyl)carbonylmethyl] dimethylammonium Chloride i) Chloroacetindolide:

To a chilled (−13° C.) solution of indoline (12 g, 100 mmol) and triethylamine (37 ml, 262 mmol) in dichloromethane (350 ml) was added dropwise a solution of chloroactyl chloride (10.6 ml, 131 mmol) in dichloromethane (250 ml). The reaction mixture was stirred at −13° C. for another 30 minutes and then allowed to warm up to room temperature. The reaction mixture was washed with water (600 ml), the aqueous layer was collected and extracted once more with dichloromethane (200 ml). The combined organic layers were dried over sodium sulfate and the solvent was evaporated in vacuo to yield the crude title compound. Purification by dry column chromatography with mixtures of ethyl acetate-hexanes as eluents followed by recrystallization from methanol provided 16 g of the title compound.

ii) Dimethylaminoacetindolide:

A mixture of chloroacetindolide (8.5 g, 43.4 mmol) in dimethylamine 40% wt. solution in water (85 ml) was refluxed for one hour. The cooled reaction mixture was partitioned between 1M NaOH aqueous solution (85 ml) and dichloromethane (170 ml). The aqueous layer was collected and extracted once more with dichloromethane (85 ml). The combined organic extracts were back-washed with water 9200 ml, 100 ml) and dried over sodium sulfate. Evaporation of the solvent in vacuo yielded 8.8 g (95% yield) of the title compound.

iii) N,N-Bis-[(1-Indolinyl)carbonylmethyl] dimethylammonium chloride:

A mixture of chloroacetindolide (1.96 g, 10 mmol), dimethylaminoacetindolide (2.04 g, 10 mmol) and potassium iodide (0.017 g, 0.1 mmol) in methanol (20 ml) was heated to 80° C. for 16 hours. To the cooled reaction mixture was added diethyl ether (20 ml). The resulting precipitate was collected and recrystallized from a mixture of methanol-diethyl ether (1:1, v/v) to yield 3.35 g (84% yield) of the title compound, characterized by elemental analysis as set forth in Table 1.

EXAMPLE 2

N-[(1-Indolinyl)carbonylmethyl]-N-(phenylcarbamoylmethyl)dimethylammonium Chloride i) Chloroacetindolide:

To a chilled (−13° C.) solution of aniline (18.2 g, 200 mmol) and triethylamine (73 ml, 520 mmol) in dichloromethane (350 ml) was added dropwise a solution of chloroactyl chloride (21.1 ml, 260 mmol) in dichloromethane (250 ml). The reaction mixture was stirred at −13° C. for another 30 minutes and then allowed to warm up to room temperature. The reaction mixture was washed with water (600 ml), the aqueous layer was collected and extracted once more with dichloromethane (200 ml). The combined organic layers were dried over sodium sulfate and the solvent was evaporated in vacuo to yield the crude title compound. Purification by dry column chromatography with mixtures of ethyl acetate-hexanes as eluents followed by recrystallization from methanol provided 29.6 g (87% yield) of the title compound.

ii) Dimethylaminoacetindolide:

See steps i and ii of Example 1.

iii) N-[(1-Indolinyl)carbonylmethyl]-N-(phenylcarbamoylmethyl)dimethylammonium Chloride:

A mixture of chloroacetindolide (1.20 g, 7.08 mmol), dimethylaminoacetindolide (1.44 g, 7.08 mmol) and potassium iodide (0.012 g, 0.071 mmol) in methanol (15 ml) was heated to 80° C. for 16 hours. To the cooled reaction mixture was added diethyl ether (15 ml). The resulting precipitate was collected and recrystallized from a mixture of methanol-diethyl ether (1:1, v/v) to yield 2.18 g (82% yield) of the title compound, characterized by elemental analysis as set forth in Table 1.

EXAMPLE 3

N-[(1-Indolinyl)carbonylmethyl]triethylammonium Chloride

I) Chloroacetindolide:

See step i of Example 1.

ii) N-[(1-Indolinyl)carbonylmethyl]triethylammonium Chloride:

A mixture of chloroacetindolide (1.8 g, 9.2 mmol), triethylamine (4.0 ml, 28.7 mmol) and potassium iodide (0.015 g, 0.092 mmol) in methanol (20 ml) was heated to 80° C. for 36 hours. To the cooled reaction mixture was added diethyl ether (50 ml). The resulting precipitate was collected and recrystallized from a mixture of methanol-acetone-diethyl ether (1:3:8, v/v/v) to yield 2.07 g (76% yield) of the title compound, characterized by elemental analysis as set forth in Table 1.

EXAMPLE 4

N,N-Bis-[(1-Naphthyl)carbonylmethyl] dimethylammonium Chloride i) Chloroacetindolide:

To a chilled (0° C.) solution of 1-naphthylamine (25 g, 174 mmol) and potassium carbonate (29 g, 209 mmol) in chloroform (150 ml) was added a solution of chloroactyl chloride (15.3 ml, 192 mmol) in chloroform (100 ml). The solid was collected, washed with water (300 ml), and then extracted with diethyl ether via Soxhlet extraction to yield 17.5 g (46% yield) of the title compound.

ii) Dimethylaminoacetyl-1-naphthylamide:

A mixture of chloroacetyl-1-naphthylamide (8.96 g, 39 mmol) in dimethylamine 40% wt. solution in water (100 ml) was refluxed for one hour. The cooled reaction mixture was partitioned between 1M NaOH aqueous solution (80 ml) and dichloromethane (100 ml). The aqueous layer was collected and extracted once more with dichloromethane (100 ml). The combined organic extracts were back-washed with water (2×50 ml) and dried over sodium sulfate. Evaporation of the solvent in vacuo yielded 8.87 g (100% yield) of the title compound.

iii) N,N-Bis-[(1-Naphthyl)carbonylmethyl] dimethylammonium Chloride:

A mixture of chloroacetyl-1-naphthylamide (6.59 g, 30 mmol), dimethylaminoacetyl-1-naphthylamide (6.85 g, 30 mmol) and potassium iodide (50 mg, 0.3 mmol) in anhydrous m-xylene (30 ml) was refluxed for 1 hour. The resulting precipitate was collected while the reaction mixture was still hot and was washed with hot portions of ethyl alcohol to yield 4.6 g (34% yield) of the title compound. TLC analysis and capillary electrophoresis of an aliquot sample show the compound to be pure.

TABLE 1

| Example # | Formula | M.W. | Calculated (%) | Found (%) |
|---|---|---|---|---|
| 1 | $C_{22}H_{26}N_3O_2Cl$ | 399.92 | C 66.07 H 6.55 N 10.51 | C 65.42 H 6.57 N 10.30 |
| 2 | $C_{20}H_{24}N_3O_2Cl$ | 373.88 | C 64.25 H 6.47 N 11.24 | C 63.91 H 6.39 N 11.13 |
| 3 | $C_{16}H_{25}N_2OCl.3H_2O$ | 350.88 | C 54.77 H 8.90 N 7.98 | C 55.97 H 8.88 N 8.09 |
| 4 | $C_{26}H_{26}N_3O_2Cl$ | 447.96 | C 69.71 H 5.85 N 9.38 | C 69.63 H 6.07 N 9.28 |

EXAMPLE 5

The following method was one of the general methods available to determine the antitussive activity of the compounds of the present invention.

Male albino Dunkin-Hartley strain guinea-pigs (weight 300–400 g) were supplied by Harlan UK Ltd., Bicester, Oxon, UK.

Figure 1:
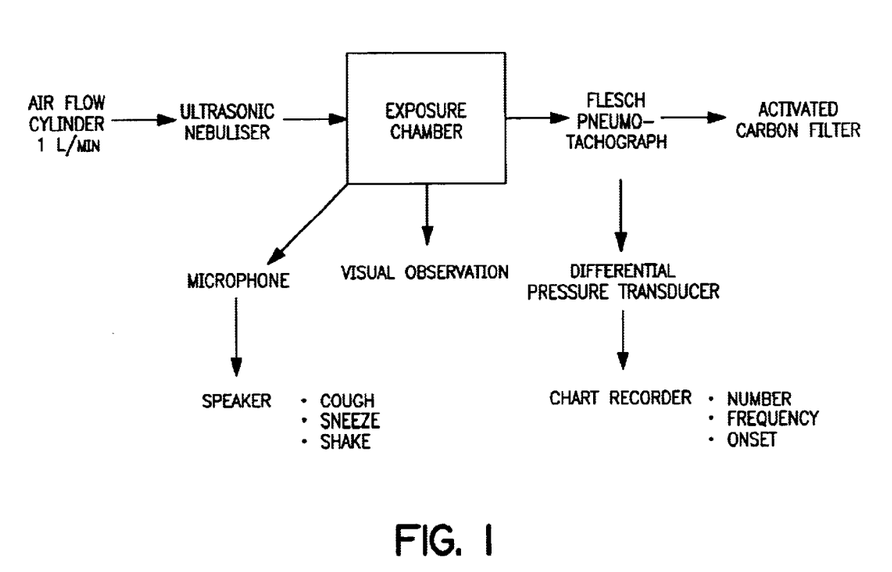
FIG. 1 is a flow diagram showing the layout of the experimental apparatus used for cough determination.

The method used was modified from that described by Adcock J. J., Schneider C. and Smith T. W., "Effects of Morphine and a Novel Opioid Pentapeptide BW443C, on Cough, Nociception and Ventilation in the Unanaesthetized Guinea-pig", *Br. J. Pharmacol.*, 93, 93–100 (1988). Individual conscious guinea-pigs were placed unrestrained into a sealed purpose built perspex exposure chamber (3,000 cm$^3$ volume) and allowed to acclimatize prior to aerosol administration. The layout of the experimental apparatus used is shown in FIG. 1.

Cylinder air was introduced into the exposure chamber at a flow rate of 1 liter/min, maintained by a needle valve and monitored by a rotameter. From the rotameter the air passed through the cup of an ultrasonic nebulizer (DeVilbis UltraNeb 2000) which was used to generate aerosols of drug or citric acid at 0.15 ml/min. A Fleisch pneumotachograph, connected to a differential pressure transducer (Grass model PT5) was attached to the outflow from the exposure chamber and provided a measurement of airflow from the chamber. The differential pressure transducer was connected to a Grass polygraph from which a hard copy record was produced. The output from the polygraph was directed to a computerized data acquisition system (Poh-Ne-Mah) for real time recording of data. A tie-clip microphone was placed in the exposure chamber and connected via a pre-amplifier to a loudspeaker output to provide the observer with an audio monitor of responses.

Cough responses were induced by exposure to an aerosol of citric acid (1M) for 10 minutes. Animals were continuously monitored by trained observer, and the number of coughs were counted during a 15 minute period from commencement of the citric acid aerosol administration. Three characteristic responses were produced by exposure to citric acid: cough, sneeze and "wet dog" shake.

Figure 2A:
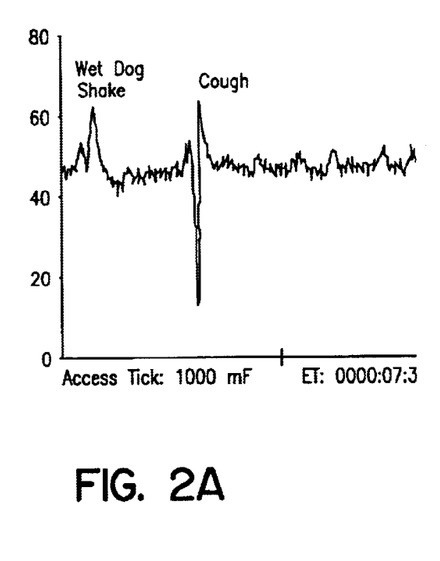
FIGS. 2A and 2B are expanded scale recordings of pressure changes derived from the differential pressure transducer during characteristic responses exhibited by a guinea-pig during exposure to an aerosol of citric acid.
Figure 2B:
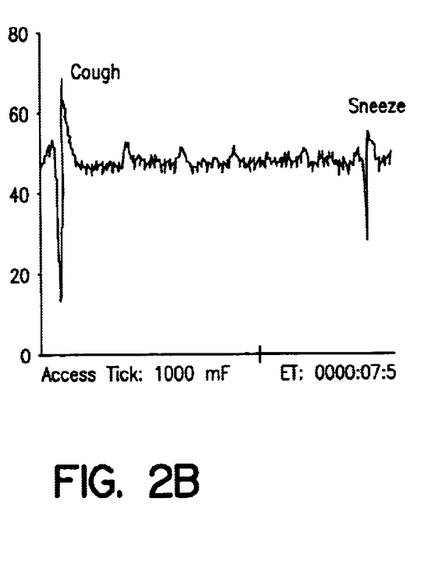

The three types of response were differentiated primarily by sound and visual observation. Confirmation of the numbers of multiple coughs was determined by reference to the change in flow rate displayed by the Poh-Ne-Mah system monitor. Printouts demonstrating the pressure changes characteristic of the different response to irritant are shown in FIGS. 2A and 2B. Data recorded for individual guinea-pigs on the Poh-Ne-Mah system was stored on an optical disk. Each cough was marked on the Grass polygraph paper trace, and from these record numbers, frequency and time of onset of coughs were determined. The cough response was defined by a characteristic coughing sound and behavior, associated with a marked biphasic pressure change. The biphasic pressure changes associated with a sneeze were not of as great a magnitude as those associated with a cough, the secondary rise in pressure also being far less than during a cough (FIG. 2B). The sound of a sneeze differed from that of a cough, and sneezing was associated with nose rubbing activity. The third response, a "wet dog" shake, produced a rise in pressure only (FIG. 2A) and lacked the definitive sound of a cough or sneeze.

Quantities of drugs were weighed out and dissolved in a vehicle. Equal volumes were aliquotted into sample tubes before being passed, together with another sample tube containing the same volume of vehicle, to an independent observer for coding. Pre-treatments were matched by concentration together with a vehicle control group. Five guinea-pigs were randomly allocated to each treatment group. Animals were pre-treated with either vehicle (0.9% sterile saline), lidocaine or test drugs for 5 minutes immediately prior to citric acid aerosol exposure. Test drugs and lidocaine were administered as aerosols at concentrations of 0.1, 1.0 and 10.0 mg/ml. The sequence of pre-treatment administration was determined according to a 4×4 Latin Square design.

Data presented as the mean ±SEM number of coughs produced by individual guinea-pigs within each group during the 15 minute observation period or mean ±SEM latency of cough were analyzed using one way analysis of variance to compare mean responses between matched groups of animals (doses) and between unmatched groups (treatments) followed by the Tukey-Kramer multiple comparison test where appropriate.

In one set of experiments using the general protocol described above, the antitussive activity of N-[(1-Indolinyl)carbonylmethyl]-N-(phenylcarbamoylmethyl) dimethylammonium chloride (Compound 2) was tested. Results showed that pre-treatment of guinea pigs with aerosols of Compound 2 at 10.0 mg/ml immediately before exposure to citric acid (1M) inhibited cough responses by 56% compared with vehicle (distilled water) pre-treated guinea pigs over the 15 minute observation period. At the same time the mean latency of cough onset was prolonged by four fold.

The antitussive activity of N-[(1-Indolinyl)carbonylmethyl]triethylammonium chloride (Compound 3) was similarly tested. Pre-treatment of guinea pigs with aerosols of Compound 3 at 10.0 mg/ml immediately before exposure to citric acid (1M) reduced cough responses by 36% compared with vehicle (distilled water) pre-treated guinea pigs over the 15 minute observation period. Results from the same experiment showed the time to the first recorded cough response elicited by citric acid was prolonged by Compound 3 pre-treatment immediately prior to citric acid exposure, when latency of cough onset increased 2.5 fold.

EXAMPLE 6

In another experiment similar to that described above in Example 5, the duration of the antitussive effects of the compounds of the present invention against citric acid-induced cough responses were investigated in conscious guinea pigs. Test agents or vehicle were administered as aerosol pre-treatments (10 mg/ml, 5 minute duration) at 5 minutes, 30 minutes, 1 hour, 2 hours and 4 hours prior to induction of cough responses by citric acid aerosol.

EXAMPLE 7

The antitussive effects of a 5 minute pre-treatment with aerosolized compounds of the present invention and lidocaine on capsaicin aerosol-induced cough were investigated in conscious guinea-pigs using a method similar to that described in Example 5.

EXAMPLE 8

Therapeutic treatment with the compounds of the present invention also can be determined by a similar method as described in Example 5. The antitussive effects of compounds of the present invention and lidocaine administered after induction of cough responses by exposure to citric acid aerosol were investigated in conscious guinea pigs. Vehicle or test agents were administered as aerosols (10 mg/ml; 5 minute duration) 2 minutes after exposure to citric acid aerosol began. Cough responses were recorded during a 15 minute observation period (t=0 to t=15 minutes) from initiation of the citric acid exposure.

EXAMPLE 9

Investigation of Antitussive Activity of Aerosolized Test Compound on Citric Acid-Induced Cough Responses in Conscious Rabbits Protocol Twenty-two male New Zealand white rabbits were randomly allocated to either of two groups of 11 rabbits.

Pairs of rabbits (control versus test) were placed in individual exposure chambers with an airflow of 5 liter/min through the chambers.

Each rabbit was exposed to ozone (3 ppm) for 1 hour.

The rabbits were then immediately exposed to aerosols of either vehicle (chamber 1) or test compound (10 mg/ml, chamber 2) at a nebulization rate of 0.9 ml/min.

Cough responses were induced with citric acid aerosol (1.6 M) Coughs were counted during the 10 minute exposure to citric acid.

All rabbits were exposed to ozone before vehicle or test drug pre-treatment.

All publications and patent applications mentioned in this specification are herein incorporated by reference to the same extent as if each individual publication or patent application was specifically and individually incorporated by reference.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound of the following formula (I), or a solvate or pharmaceutically acceptable salt thereof:

(I)

wherein Y and E are independently selected from a group represented by the following formula (II):

(II)

wherein R, $R_1$, $R_2$ and $R_3$ are independently selected from hydrogen, $C_1$–$C_8$ alkyl and $C_3$–$C_8$ alkoxyalkyl; m is 1; A is the ring system of formula (IX):

(IX)

where $R_{12}$ is selected from bromine, chlorine, fluorine, carboxy, hydrogen, hydroxy, hydroxymethyl, trifluoromethyl, $C_2$–$C_7$ alkanoyloxy, $C_1$–$C_6$ alkyl, $C_1$–$C_6$ alkoxy, and $C_2$–$C_7$ alkoxycarbonyl, Z is N and X is a direct bond to Z; An is the acid addition salt of a pharmaceutically acceptable acid or the anion from a pharmaceutically acceptable salt, and isolated enantiomeric, diastereomeric and geometric isomers thereof, and mixtures thereof.

2. A pharmaceutical composition for the treatment and/or prevention of cough, comprising an effective amount of a compound according to claim 1 and a pharmaceutically acceptable carrier, diluent or excipient.

* * * * *